US00PP13113P2

(12) United States Plant Patent
Carruth

(10) Patent No.: US PP13,113 P2
(45) Date of Patent: Oct. 22, 2002

(54) SHRUB ROSE PLANT NAMED 'WEKPIPOGOP'

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 09/754,412

(22) Filed: Jan. 2, 2001

(51) Int. Cl.[7] ..... A01H 5/00
(52) U.S. Cl. ..... Plt./103
(58) Field of Search ..... Plt./103

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new variety of Shrub rose suitable for garden decoration, having flowers of bright white coloration.

1 Drawing Sheet

BOTANICAL CLASSIFICATION

*Rosa hybrida.*

VARIETY DENOMINATION

'Wekpipogop'.

BACKGROUND OF THE INVENTION

This invention relates to a new and distinct variety of Shrub Rose. The varietal denomination of the new variety is *Rosa hybrida* cv. 'WEKpipogop'. It has as its seed parent the variety known as 'JACship' (U.S. Plant Pat. No. 7,948) and as its pollen parent the variety known as 'WEOpop' (U.S. Plant Pat. No. 6,809).

SUMMARY OF THE INVENTION

Among the features which distinguish the new variety from other presently available and commercial rose cultivars known to the inventor are the following combination of characteristics: its large clusters of white flowers, its rough under side of the rachis, its very full branching and rounded mature growth habit and its honey to anis-like fragrance. The plant has a rounded and very bushy growth habit, suitable for garden decoration.

Asexual reproduction of the new variety by budding as performed in Kern County and Upland, Calif., shows that the foregoing and other distinguishing characteristics come true to form and are established and transmitted through succeeding propagations. 'WEKpipogop' may be asexually propagated by cuttings, budding and grafting.

Comparison with Parents

The new rose may be distinguished from its seed parent, 'JACship' by the following combination of characteristics: whereas 'WEKpipogop' bears medium sized flowers of bright white coloration with double petalage (about 24 to about 28), 'JACship' bears significantly larger flowers of pink coloration with heavier petalage (about 45). The seed parent has a bushy upright mature growth habit, whereas the new variety has a more rounded mature growth habit.

The new variety may be distinguished from its pollen parent, 'WEOpop' by the following combination of characteristics: whereas 'WEKpipogop' bears medium sized flowers (about 5.1 to about 5.5 cms. in diameter), 'WEOpop' bears significantly smaller flowers (about 2.5 to about 3 cms. in diameter). The pollen parent bears small foliage (about 4.8 to about 6.9 cms. in length and about 3.9 to about 6.3 cms. in width at the widest point), whereas 'WEKpipogop' bears bigger foliage (about 7.6 to about 8.9 cms. in length and about 6.3 to about 7.0 cms. in width at the widest point). The pollen parent has a shorter rounded mature growth habit, whereas the new variety has a significantly larger mature growth habit.

BRIEF DESCRIPTION OF THE ILLUSTRATION

The accompanying photograph illustrates 3 to 4 year old rose plants of the new variety and shows the flowering thereof from bud to full bloom depicted in color as nearly correct as it is possible to make in a color illustration of the character. Throughout this specification, color values are based upon the Colour Chart of The Royal Horticultural Society of London, England, (1995 ed.) except where common terms of color definition are employed.

DESCRIPTION OF THE NEW VARIETY

The following description is of 3 to 4 year old rose plants of the new cultivar grown outdoors in Upland, Calif. in the month of October. Phenotypic expression may vary with environmental, cultural and climatic conditions, as well as differences in conditions of light and soil.

FLOWER

The new variety usually bears its flowers in clusters of four to five or more per stem. Flowers are borne in moderately rounded clutsters on somewhat pendulous medium length stems (about 19 to about 30 cms.). Outdoors, the plant blooms very abundantly and nearly continuously during the growing season. The flowers have a moderate anise-like to honey fragrance.

BUD

The peduncle is about 2.2 to about 3.8 cms. in length, of slender to average caliper and usually erect. It is moderately rough, with many stipitate glands and some hairs. Peduncle color is between 147B and 144B sometimes lightly suffused on the side exposed to the sun with between 185B and 184B.

Before the calyx breaks, the bud is about 0.8 to about 1.2 cms. in diameter at the widest point, about 0.9 to about 1.3 cms. in length and very ovoid to somewhat pointed in shape with a moderately conspicuous neck. The surface of the bud bears some slender foliaceous appendages and many stipitate glands, usually with slender entire foliaceous parts extending beyond the tip of the bud about ¼ of its length. Bud color is between 144A and 147B sometimes lightly suffused on the side exposed to the sun with between 185B and 184B.

The inner surface of the sepals is covered with fine wooly tomentum; sepal margins are lined with many stipitate glands and hairs.

As the petals open (after the calyx breaks), the bud is about 0.9 to about 1.5 cms. in diameter at the widest point, about 1.2 to about 1.9 cms. in length, and moderately ovoid to pointed in form. The color of the under and upper surfaces of the newly opened petals is between 11C and 11D. On the under surface, at the point where the petal attaches, there is a very small zone of near 12C. On the upper side, at the point where the petal attaches, there is a small zone of near 13B.

BLOOM

When fully open, the bloom ranges from about 4.2 to about 6.5 cms. in diameter. Petalage is double with about 24 to 28 petals and about 1 to 8 petaloids arranged irregularly. When partially open, the bloom form is moderately cupped to globular and the petals are loosely spiraled to cupped with petal edges slightly reflexed outward. When fully open, the bloom form is more cupped, and the petals are more loosely cupped with petal edges somewhat reflexed outward.

PETALS

The substance of the petals is moderate and of medium thickness, with upper surfaces somewhat stainy and under surfaces somewhat shiny. The outer petals are nearly rounded in shape with apices moderately rounded, sometimes slightly notched with one notch. The inner petals are more broadly obovate to round in shape with apices somewhat rounded, sometimes slightly notched with one notch. The petal margin is entire. Petals are about 1.5 to about 2.4 cms in length and about 1.1 to about 1.9 cms in width at the widest point.

NEWLY OPENED FLOWER

The under and upper surface of the outer petals is between 155D and 11D. At the point where the petal attaches, there is a very small zone of between 11D and 13D.

The under and upper surface of the intermediate and the inner petals is between 8D and 11D.

The general tonality of the newly opened flower is between 8D and 11D with the outermost petal near 155D.

THREE-DAY-OLD FLOWER

The under and upper surface of the outer and inner petals is between 155B and 155D. There is no visible change in coloration at the point where the petal attaches.

The general tonality of the three-day-old flower is between 155B and 155D.

On the spent bloom, the petals usually drop off cleanly.

In October in Upland, Calif., blooms on the bush growing outdoors generally last about four to five days. Cut roses from plants grown outdoors and kept at normal indoor living temperatures generally last about four to five or more days.

MALE REPRODUCTIVE ORGANS

Stamens are average in number (average about 60) and are arranged regularly about the pistils; a few are mixed with petaloids. The filaments are irregular in length, most with anthers. Filaments are between 12B and 14B in color. The anthers open approximately at the same time. Anther color when immature is between 15A and 21B. Anther color at maturity is between 164A and 165B. Pollen is somewhat sparse and near 11D in color.

FEMALE REPRODUCTIVE ORGANS

Pistils vary in number (average about 20). The styles are somewhat even, moderately short in length, very thin in caliper, and somewhat bunched. Stigma color is between 4C and 9D. Style color is between 4D and 4C. Ovaries are usually all enclosed in the calyx.

Hips have not appeared on this variety when grown in Upland, Calif.

FOLIAGE

The compound leaves are usually comprised of three to seven leaflets and are borne abundantly. The seven-leaflet leaves are about 9.5 to about 12.0 cms. in length and about 7.0 to about 10.5 cms. in width at the widest point, of medium thickness, leathery in texture and semi-glossy to glossy in finish. The terminal leaflets are about 3.1 to about 5.9 cms. in length and about 1.9 to about 3.2 cms. in width at the widest point, shaped oval to somewhat ovate with acute apices and moderately acute to somewhat rounded bases. Their margins are usually simply serrate.

The upper surface of the mature leaf is between 147A and 137A. The under surface of the mature leaf is between 138A and 147B. The upper and under surface of the young leaf is between 144A and 146C, often moderately suffused with between 183B and 187B.

The rachis is somewhat light in caliper and moderately rough. The upper side is somewhat shallowly grooved with many hairs and few stipitate glands on the edges of the grooves. The under side of the rachis is moderately rough with some hairs, few stipitate glands and few very small prickles.

The stipules are about 0.6 to about 1.1 cms. in length and somewhat narrow to medium in width with straight points that usually turn out at an angle of less than 45 degrees.

The plant displays an average degree of resistance to powdery mildew and rust as compared to other commercial varieties grown under comparable conditions in Upland, Calif.

GROWTH

The plant has a rounded and very bushy medium height growth habit (about 140 to about 160 cms. in height and about 125 to about 140 cms. spread at the widest point), with very full branching. It displays a vigorous growth and the canes are medium to heavy caliper. The sepals are about 1.4 to about 2.5 cms in length and about 0.5 to about 0.8 cm in width at the widest point. The under surface of the sepal is between 144A and 147B, sometimes slightly suffused on the side exposed to the sun with between 185B and 184B. The upper surface of the sepal is between 139C and 148D. The petiole is about 0.9 to about 1.3 cms in length and about 0.1 cm in diameter at the widest point. The petiole color is between 138A and 147B. As indicated by the USDA Plant Hardiness Zone Map, the plant's winter hardiness is between zones 5b and 6a. The plant's drought/heat tolerance is yet to be determined. Root initiation can vary between about 10 to 21 days. Temperature, age of the cutting wood and time of the year are variables.

The color of the major stems is between 146C and 146B. They bear some large prickles that are about 0.5 to about 0.7 cms. in length. The large prickles are angled to somewhat hooked downward with a medium length somewhat broad base; prickle color is between 165A and 166A. The major stem bears no small prickles.

The color of the branches is between 137A and 146B. The branches bear some large prickles of similar shape; prickle color is between 173B and 180B. They bear few small prickles of similar shape and coloration and a few fine coarse hairs.

The color of the new shoots is between 144A and 146C often lightly suffused with between 183B and 187B. The shoots bear few large prickles of similar shape and which are between 184A and 183B in color. They bear few small prickles of similar shape and coloration and few fine coarse hairs.

I claim:

1. A new and distinct Shrub rose plant of the variety substantially as described and illustrated herein.

* * * * *

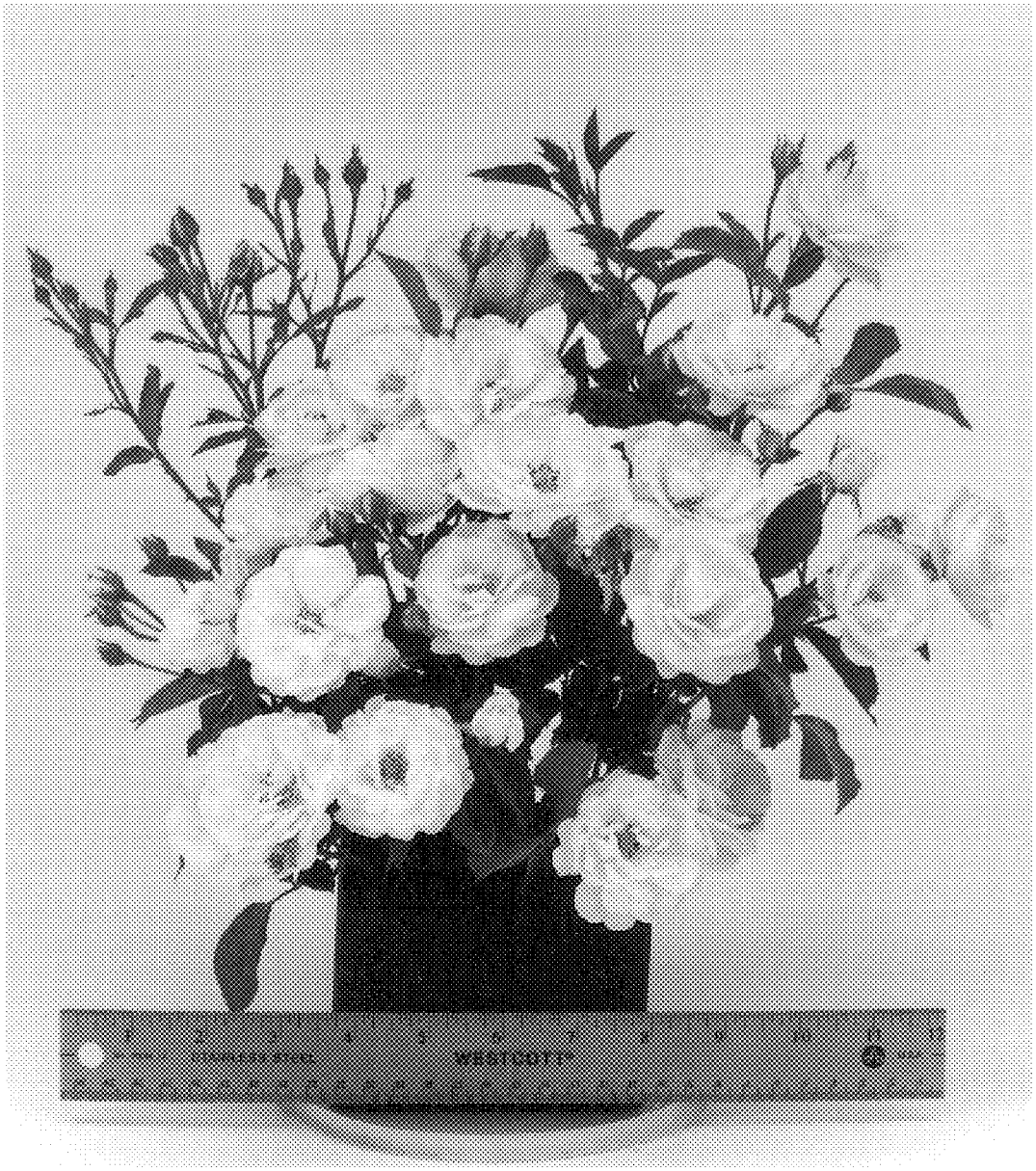
WESTCRIFT